(12) United States Patent
Sahin et al.

(10) Patent No.: US 11,911,713 B2
(45) Date of Patent: Feb. 27, 2024

(54) EXOSOME ISOLATION METHOD BY TWO PHASE FLUID SYSTEM

(71) Applicant: YEDITEPE UNIVERSITESI, Istanbul (TR)

(72) Inventors: Fikrettin Sahin, Istanbul (AR); Pakize Neslihan Tasli, Istanbul (AR); Oguz Kaan Kirbas, Istanbul (AR); Batuhan Turhan Bozkurt, Istanbul (AR)

(73) Assignee: YEDITEPE UNIVERSITESI, Istanbul (TR)

( * ) Notice: Subject to any disclaimer, the term of this patent is extended or adjusted under 35 U.S.C. 154(b) by 864 days.

(21) Appl. No.: 16/969,997

(22) PCT Filed: Feb. 15, 2019

(86) PCT No.: PCT/TR2019/050103
§ 371 (c)(1),
(2) Date: Aug. 14, 2020

(87) PCT Pub. No.: WO2019/160519
PCT Pub. Date: Aug. 22, 2019

(65) Prior Publication Data
US 2021/0101093 A1    Apr. 8, 2021

(30) Foreign Application Priority Data

Feb. 15, 2018   (TR) .................................. 2018/02164

(51) Int. Cl.
*B01D 15/34*     (2006.01)
*A61K 35/16*     (2015.01)
(Continued)

(52) U.S. Cl.
CPC .............. *B01D 15/34* (2013.01); *A61K 35/16* (2013.01); *A61K 35/20* (2013.01); *A61K 35/22* (2013.01);
(Continued)

(58) Field of Classification Search
CPC ........ A61K 35/52; A61K 35/50; A61K 35/38; A61K 35/22; A61K 35/20; A61K 35/16; B01D 15/34
See application file for complete search history.

(56) References Cited

U.S. PATENT DOCUMENTS 6,899,863 B1    5/2005 Dhellin et al.

FOREIGN PATENT DOCUMENTS

EP         3279332 A1    2/2018

OTHER PUBLICATIONS

Anna-Kristin Ludwig et al., Exosomes: Small vesicles participating in intercellular communication, The International Journal of Biochemistry & Cell Biology, 2012, pp. 11-15, 44.
(Continued)

*Primary Examiner* — Jennifer Wecker
*Assistant Examiner* — Kathryn Elizabeth Limbaugh
(74) *Attorney, Agent, or Firm* — Bayramoglu Law Offices LLC

(57) ABSTRACT

The present invention is an exosome isolation method for obtaining high purity exosomes inexpensively from samples of large and small amounts and types of samples from which exosomes could not be obtained before such as plant lysates. The exosome isolation method incorporates a two phase fluid extraction system, and includes the steps of isolation using dextran and PEG for removing proteins and undesired substances therein, and the steps of washing and dextran removal to collect exosomes in a pure form.

21 Claims, 7 Drawing Sheets

(51) Int. Cl.
- A61K 35/20 (2006.01)
- A61K 35/22 (2015.01)
- A61K 35/38 (2015.01)
- A61K 35/50 (2015.01)
- A61K 35/52 (2015.01)

(52) U.S. Cl.
CPC .............. *A61K 35/38* (2013.01); *A61K 35/50* (2013.01); *A61K 35/52* (2013.01)

(56) References Cited

OTHER PUBLICATIONS

Nunzio Iraci et al., Focus on Extracellular Vesicles: Physiological Role and Signalling Properties of Extracellular Membrane Vesicles, International Journal of Molecular Sciences, 2016, pp. 1-32, 17, 171.

B. Stegmayr et al., Promotive Effect on Human Sperm Progressive Motility by Prostasomes, Urological Research, 1982, pp. 253-257, 10.

Yoshihiro Nakamura et al., Mesenchymal-stem-cell-derived exosomes accelerate skeletal muscle regeneration, FEBS Letters, 2015, pp. 1257-1265, vol. 589, Issue 11.

Cheau Yih Tan et al., Mesenchymal stem cell-derived exosomes promote hepatic regeneration in drug-induced liver injury models, Stem Cell Research & Therapy, 2014, pp. 1-14, 5:76.

Yuji S. Takeda et al., Neuronal Differentiation of Human Mesenchymal Stem Cells Using Exosomes Derived from Differentiating Neuronal Cells, PLOS ONE, Aug. 6, 2015, pp. 1-15, 10(8).

Stefania Raimondo et al., Citrus limon-derived nanovesicles inhibit cancer cell proliferation and suppress CML xenograft growth by inducing TRAIL-mediated cell death, Oncotarget, 2015, pp. 19514-19527, vol. 6, No. 23.

Aled Clayton et al., Analysis of antigen presenting cell derived exosomes, based on immuno-magnetic isolation and flow cytometry, Journal of Immunological Methods, 2001, pp. 163-174, 247.

M. Lucrecia Alvarez et al., Comparison of protein, microRNA, and mRNA yields using different methods of urinary exosome isolation for the discovery of kidney disease biomarkers, Kidney International, 2012, pp. 1024-1032, 82.

Jongmin Kim et al., Isolation of High-Purity Extracellular Vesicles by Extracting Proteins Using Aqueous Two-Phase System, PLOS ONE, Jun. 19, 2015, pp. 1-16, 10(6).

Hyunwoo Shin et al., High-yield isolation of extracellular vesicles using aqueous two-phase system, Scientific Reports, Aug. 14, 2015, pp. 1-11, 5:13103.

EXOSOME ISOLATION METHOD BY TWO PHASE FLUID SYSTEM

CROSS REFERENCE TO THE RELATED APPLICATIONS

This application is the national phase entry of International Application No. PCT/TR2019/050103, filed on Feb. 15, 2019, which is based upon and claims priority to Turkish Patent Application No. 2018/02164, filed on Feb. 15, 2018, the entire contents of which are incorporated herein by reference.

TECHNICAL FIELD

The present invention is an exosome isolation method which enables to obtain high purity exosomes inexpensively from samples of large and small amounts and types of samples from which exosomes could not be obtained before.

BACKGROUND

The vesicles are small sacs which are involved in the transport and storage of substances within the cell and are separated by at least one lipid bilayer from the cytoplasm fluid. Exosomes are vesicles which are released by many organisms from prokaryotes to high eukaryotes and plants and which contain lipid bilayer vesicles of different sizes [1]. The importance of these vesicles lies behind the capacity of transferring information to the other cells in order to influence the cell function. Signal transfer via exosomes is carried out by means of biomolecules in many different categories consisting of proteins, lipids, nucleic acid and sugars [2].

Functional interactions of extracellular vesicles with cells were first found in 1982 upon determining experimentally that vesicles isolated from seminal plasma increase sperm motility [3]. From this point on, studies have been conducted in many different tissues until today on the developments related to the molecular mechanism of vesicles and bringing the issues left in the dark into light.

The exosomes of mesenchymal stem cells obtained from bone marrow tissue have been shown to promote myogenic differentiation and angiogenesis in the C2C12 myoblast cell line and in C57BL/6 mice as a cardiotoxin muscle injury model, and thereby inducing regeneration into skeletal muscles [4]. The exosomes of mesenchymal stem cells obtained from endometrial tissue have been shown to decrease the ALT and AST values in serum in TAMH and THLE-2 hepatocyte cell lines and C57BL/6 mice as a $CCl_4$-induced liver injury model, and increase the activities of the genes that enable cell renewal in the liver [5]. Exosomes isolated from the PC-12 cell line undergoing cellular differentiation have been shown to increase the expression of neuronal proteins and genes of the mesenchymal stem cells, in particular miR-125b, and induce neurogenic differentiation of the mesenchymal stem cells [6]. Exosomes isolated from lemon juice have been shown to lead the cell to apoptosis on the TRAIL pathway in A549, SW480 and LAMA84 cell lines and NOD/SCID mice and to increase the activation of the apoptotic genes at a high rate. In addition, the plant-derived exosomes were isolated in a very low yield of 600 micrograms from 240 ml of sample using ultracentrifuge [7]. Exosomes isolated from antigen-presenting cells (APC) were obtained as high purity exosomes using magnetic beads coated with monoclonal antibodies specific for HLA, DP, DQ, DR, based on immunomagnetic isolation [8]. Polymeric precipitation was used as a new method to for isolation of urinary exosomes. It was found to be an easier method than the previously used methods, but it was determined that there was an excess amount of contaminant besides the exosomes [9].

The applications in the state of the art can be stated under 3 basic method titles: Ultracentrifuge based methods, Filtration based methods, Solubility-Precipitation based methods.

Ultracentrifuge based methods: Centrifugation at 100,000 g and higher speeds is the most commonly used exosome isolation method today. In addition to being a very expensive, laborious and time consuming method, it isolates the exosomes with low efficiency. This is because ultracentrifuge based methods do not have any selectivity. Since they precipitate all particles above a certain particle size, they also isolate many undesired substances such as proteins and lipoproteins, as well as the exosomes. It is not efficient in diagnostic cases (e.g. blood) because ultracentrifugation cannot be applied to samples below 50 ml; but it also does not meet the requirements when large-scale production is required. Even methods that exponentially increase the processing time, such as gradient ultracentrifugation, perform exosome isolation with much less efficiency than the invention of the present application. The invention disclosed in the patent document no. U.S. Pat. No. 6,899,863B1 is an example of this method.

Filtration based methods: It is possible to isolate exosomes with filters prepared according to the sizes of the exosomes. Although with these methods, exosomes can be obtained faster and with devices that are less costly than ultracentrifugation, this method is not preferred because the forces applied on the exosomes to pass through these small filters cause their structure to deteriorate and disintegrate. At the same time, the fact that the sizes of the exosomes are heterogeneous (e.g. the plant exosomes are larger than the animal exosomes) makes it difficult to apply the method to different exosomes and also cause frequent clogging of the filters, thereby reducing the lifetime of the filter, prolonging the process and reducing the amount of product obtained. The reason why researchers prefer filtration instead of ultracentrifuge is the advantage of speed and price. Example publication; (doi: 10.1152/ajprenal.00434.2006)

Solubility-Precipitation based methods: Exosomes can be precipitated in solutions where their solubility is low without any need for ultracentrifugation. Polymers such as polyethylene glycol (PEG) used in these methods retains the water molecules and enable precipitation of the molecules with lower-solubility including the exosomes. In order for the precipitation to be successful, the material to be isolated must be kept in PEG (or similar polymers) at 4° C. for up to 12 hours. Furthermore, other materials that precipitate besides the exosomes decrease the purity of the end product and as the exosomes are precipitated from the liquid to the solid phase, the exosome loss is much more compared to the other methods.

The problems related to the state of the art applications can be listed as follows:

The required initial volume for the ultracentrifuge method is too high,

Ultracentrifugation device is an expensive equipment and it has to be operated for long periods of time for isolation.

To be able to obtain a pure sample by ultracentrifugation method, additional time consuming processes such as washing and density difference centrifugation should be included, The product obtained by ultracentrifugation and immunomagnetic beads is obtained at very low efficiency relative to the initial amount, The separation of the monoclonal antibodies used in isolation from the exosomes is difficult and this process causes the surface proteins on the vesicular membrane structure to lose their function, Exosomes isolated by polymeric precipitation require long periods of incubation, In the polymeric precipitation method the exosomes cannot be separated from the other contaminant particles in the solution and thereby producing a heterogeneous product.

SUMMARY

The objective of the invention is to provide an exosome isolation method which enables to obtain exosomes from large and small amounts of different materials in pure form and in an inexpensive and easy manner. Furthermore, the invention enables to obtain exosomes from samples such as plant lysates from which exosomes cannot be isolated by the current techniques.

BRIEF DESCRIPTION OF THE DRAWINGS

"Exosome isolation method with two phase fluid system" developed to fulfill the objective of the present invention is illustrated in the accompanying figures, in which:

FIG. 1A is a representation of the morphologies and sizes of the exosomes obtained from different materials by SEM image. FIG. 1B is a representation of flow cytometry graph measured by CD9, CD63 and HSP70 antibodies, which are exosome characterization markers, by flow cytometry device. FIG. 1C is a representation of exosome diameter measurement graph.

FIG. 2A is a representation of the morphologies and sizes of the exosomes obtained from different materials by SEM image. FIG. 2B is a representation of flow cytometry graph measured by CD9, CD63 and HSP70 antibodies, which are exosome characterization markers, by flow cytometry device. FIG. 2C is a representation of exosome diameter measurement graph.

FIG. 3A is a representation of the morphologies and sizes of the exosomes obtained from different materials by SEM image. FIG. 3B is a representation of flow cytometry graph measured by CD9, CD63 and HSP70 antibodies, which are exosome characterization markers, by flow cytometry device. FIG. 3C is a representation of exosome diameter measurement graph.

DETAILED DESCRIPTION OF THE EMBODIMENTS

Figure 1A:
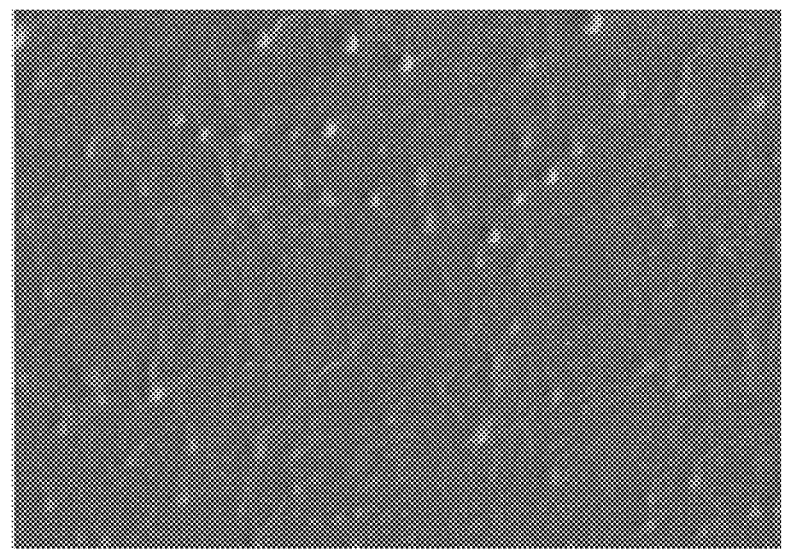
FIGS. 1A-1C show the representation of characterization of the exosome isolated from the plant lysates in the scope of the present invention.

The exosome isolation method by two phase fluid system of the present invention enables to obtain exosomes from cytoplasm inner and outer fluids, and comprises the steps of i. preparing a fluid sample containing exosomes, j. removing the contaminants within the fluid sample (the term contaminant refers to all substances besides the exosomes. These include materials such as fatty acids, proteins, nucleic acids, salts, cellular components), k. mixing the fluid sample with the isolation solution containing PEG and dextran, l. separating the mixture formed for isolation into two phases by means of the two phase fluid extraction system, m. discarding the supernatant of the sample, which is separated into two phases, in order to remove the proteins and other undesired substances therein, n. mixing the collected the phase with a washing solution, o. separating the mixture formed for washing into two phases by means of the two phase fluid extraction system, p. discarding the supernatant of the two phases that are formed and collecting the lower phase containing the exosome.

In one embodiment of the invention, the fluid sample containing exosomes is a polar fluid. This fluid sample is selected from a group comprising cell culture medium, blood, blood serum, blood plasma, placental fluid, saliva, urea, semen, breast milk, plant extract and mixtures thereof. Filtration or centrifugation method is used to remove the large contaminants from the fluid sample.

In one embodiment of the invention, the molecular weight of PEG in the isolation solution is between 25,000 and 45,000, while the molecular weight of Dextran is between 450,000 and 650,000. The concentration by mass of PEG used in the isolation solution is between 2% and 4% while the concentration by mass of Dextran is between 0.75% and 2.80%.

In one embodiment of the invention, the centrifugation method is used in the two phase separation used to obtain exosomes. This centrifugation method is performed between 1000 g and 5000 g.

In one embodiment of the invention, PEG in water is used as the washing solution, and the PEG content is between 2% and 4% by mass. The molecular weight of PEG is between 25,000 and 45,000. The centrifugation method is used to separate the washing solution into two separate phases and filtration is used to remove the microvesicles in the sample washed with the washing solution.

In one embodiment of the invention, following the step of "discarding the supernatant of the two phases that are formed and collecting the lower phase containing the exosome", the dextran removal method comprising the following sub-steps is performed for removing dextran from the obtained exosome solution:

e. adding purification solution containing monohydric alcohol or acetone in order to remove dextran from the collected lower phase, f. removing dextran from the collected lower phase via filtration, g. removing the dextran that is precipitated by the purification solution from the exosomes, h. removing the purification solution from the exosomes thereby obtaining pure exosomes (in this step, dextran is precipitated by centrifugation, the liquid phase containing exosome in the supernatant is collected and thus dextran is removed).

Ethanol or methanol can be used as the monohydric alcohol in the purification solution used to precipitate the dextran in the dextran removal method. The mixing ratio of the added alcohol with the sample is kept in the range of 1:1 to 3:1 by volume. Centrifugation method is used to remove dextran from the exosomes. The pore diameter of the filter used in the filtering process for removal of dextran is smaller than the diameter of the exosomes and greater than the molecular diameter of dextran; and the pore diameter of the filter used in the filtering process may be in the range of 40 kilodaltons to 500 kilodaltons.

The exosome isolation method of the present invention relates to developing a method isolating exosomes from large and small amounts of different materials in pure form and in an inexpensive and easy manner. In the exosome isolation method of the present invention, the materials from which the exosome is to be isolated may vary. These can be all kinds of biological materials from microbiological cultures such as bacteria, fungi, yeast, mold; and mammalian cell tissues such as fat, brain, cartilage, bone marrow, connective tissue, skin. The process steps used to prepare different materials for the isolation process can be described as follows:

A purer and more homogenous solution is obtained prior to two phase separation process by means of centrifugation performed between 7,500 g and 20,000 g for 5-20 minutes for isolation of exosomes from cell culture media, blood plasma and plant lysate. As a result, possible impurities in the dextran phase in the two phase system are avoided.

The large size particles resulting from plant disintegration by centrifugation performed between 2,000 g and 10,000 g for 5-20 minutes for exosome isolation from plant lysate are intended not to cause any impurities in the dextran phase upon precipitating due to the centrifugation applied during the two phase separation process and their weights. In addition, it is ensured that the filter, which is used during the filtration process carried out for removing particles sized 220 nanometers and above, is not clogged.

Figure 1B:
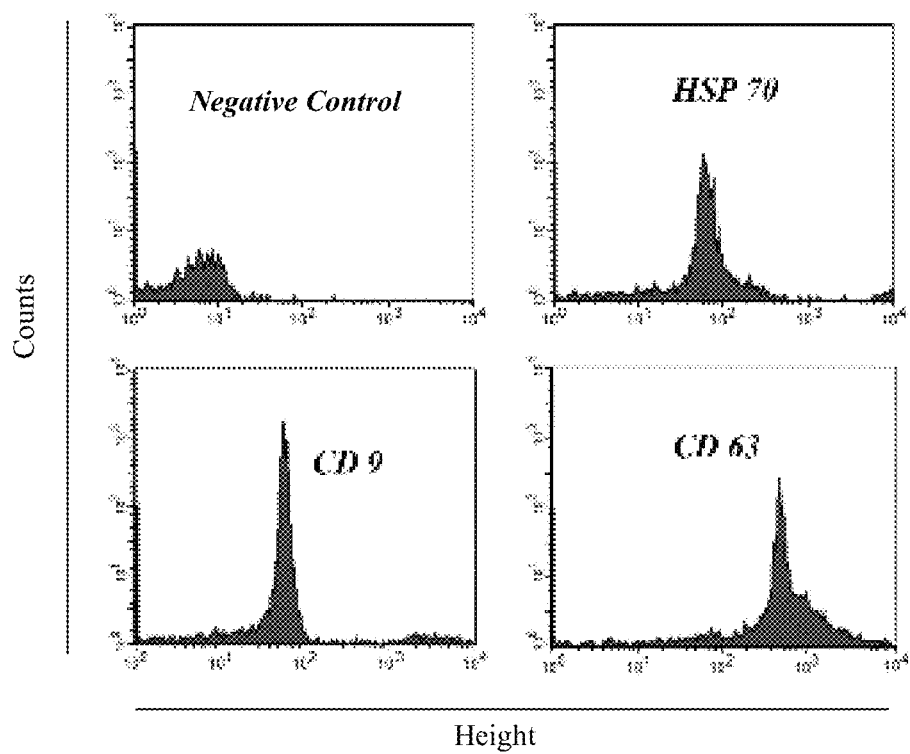
Figure 1C:
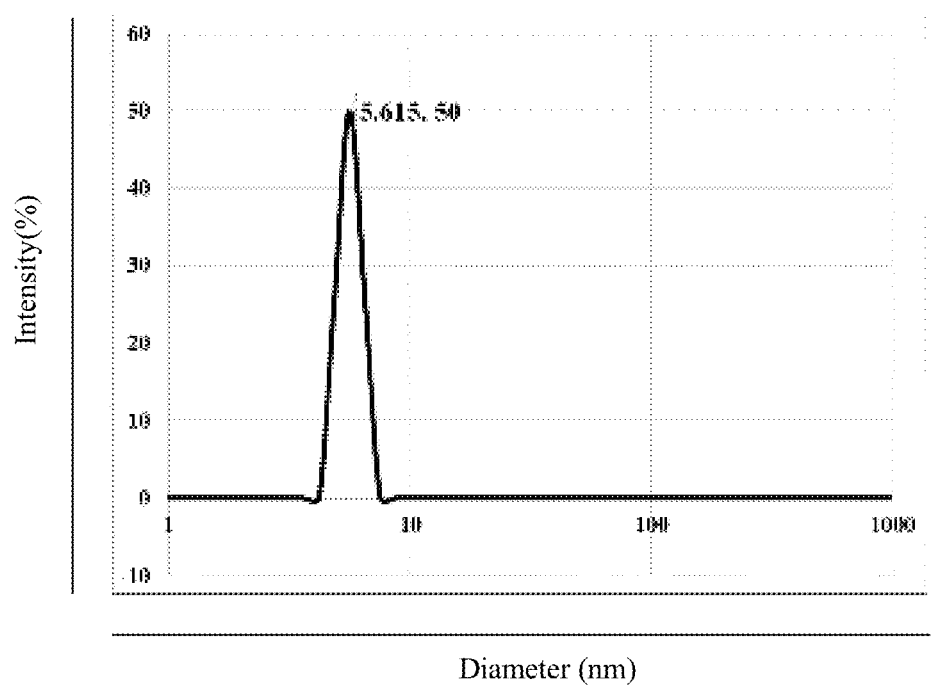
Figure 2A:
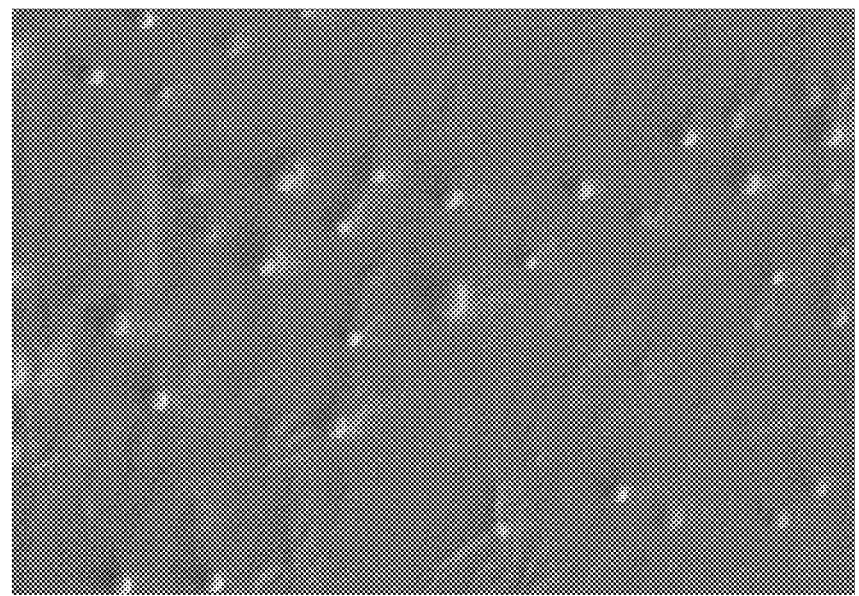
FIGS. 2A-2C show the representation of characterization of the exosome isolated from the blood plasma in the scope of the present invention.
Figure 2B:
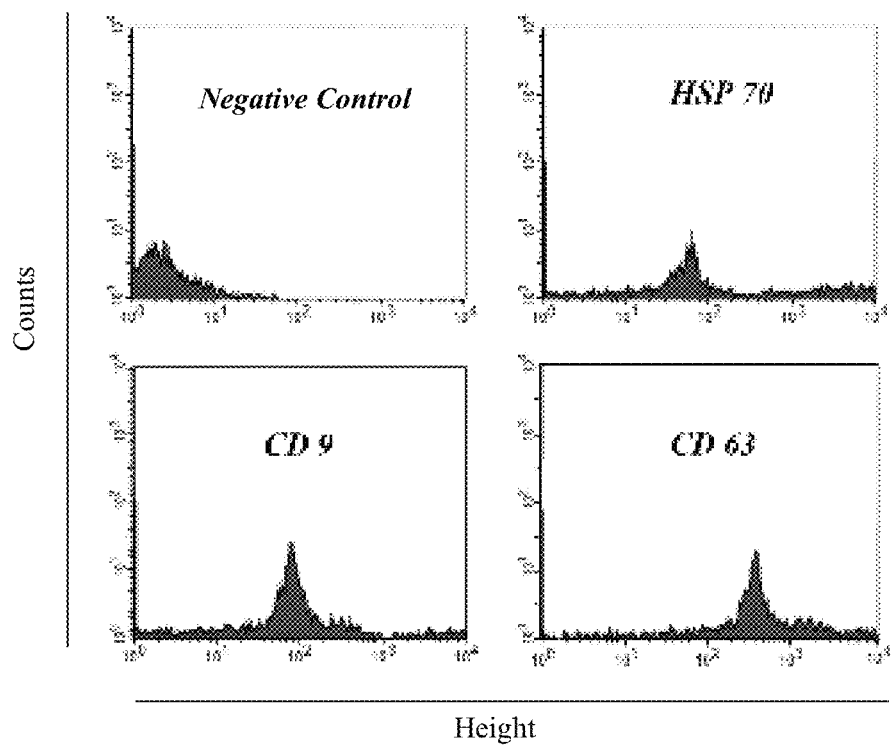
Figure 2C:
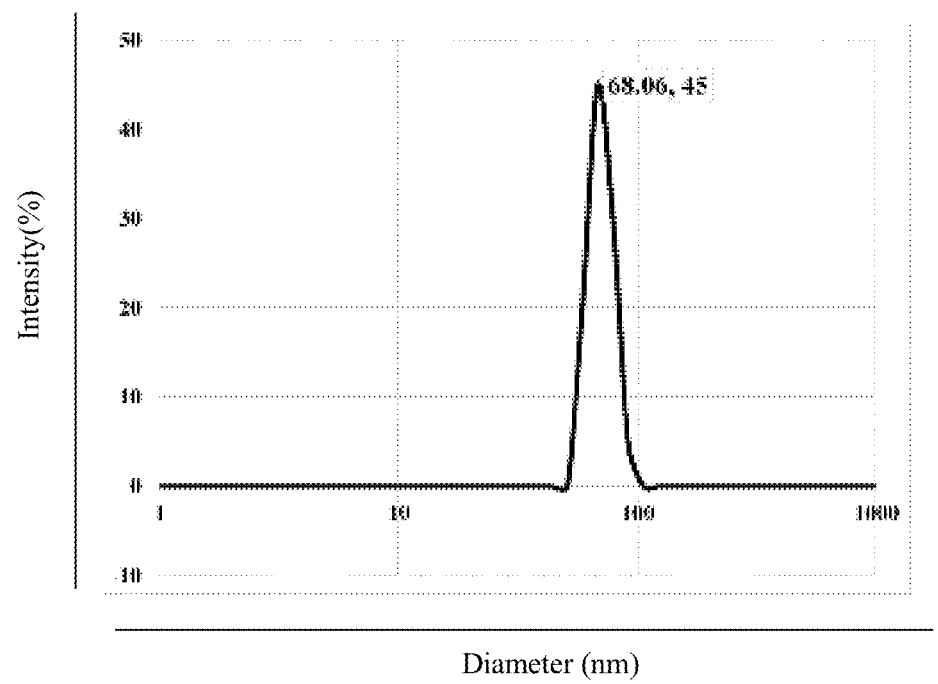
Figure 3A:
FIGS. 3A-3C show the representation of characterization of the exosome isolated from the cell culture medium in the scope of the present invention.
Figure 3B:
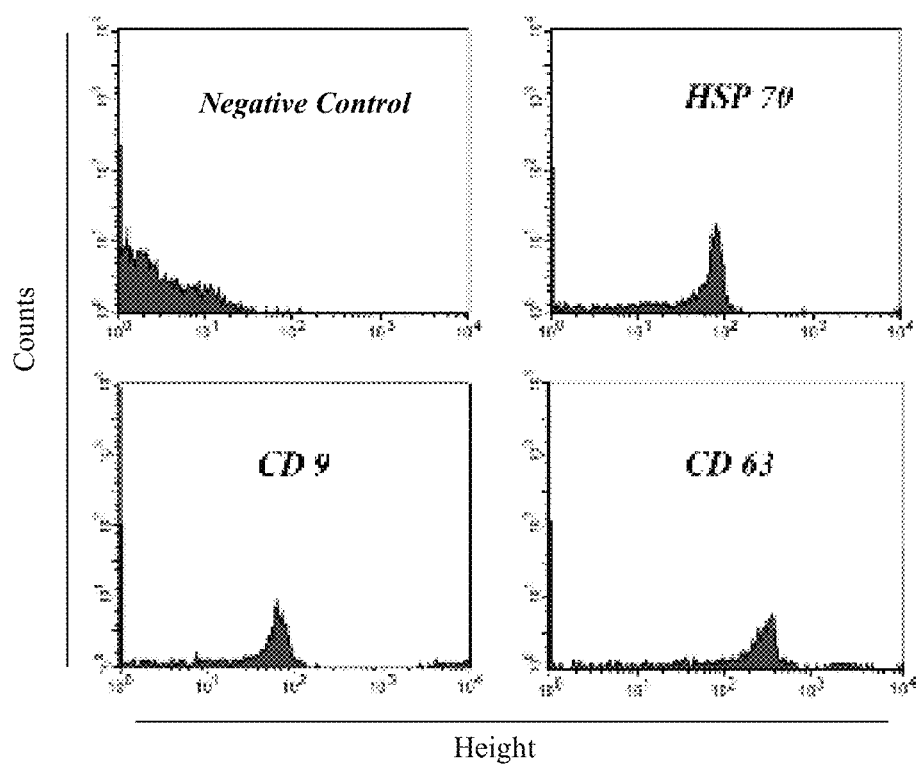
Figure 3C:
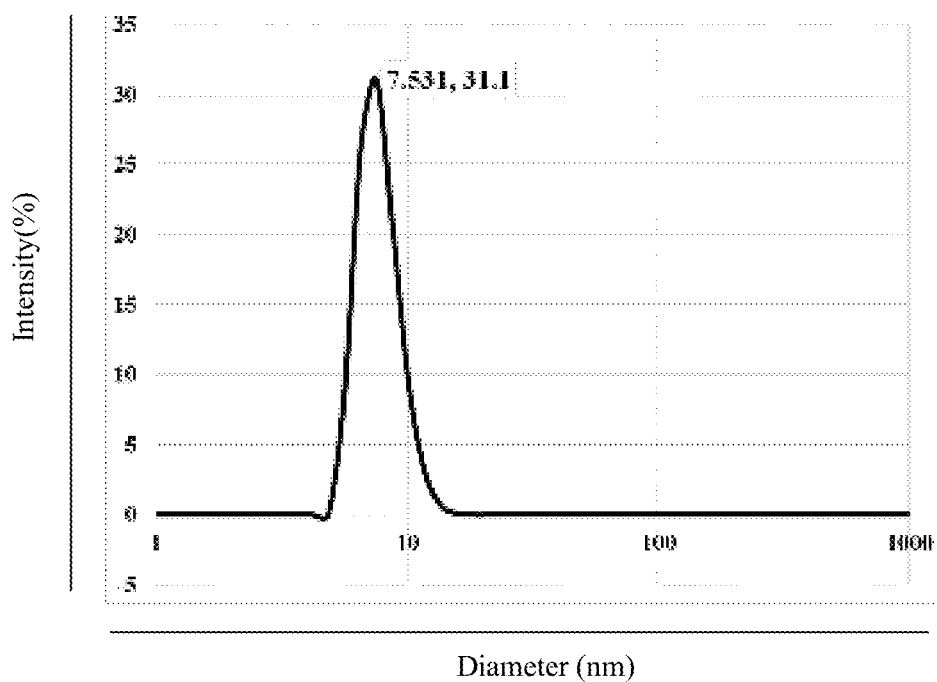
Figure 4:
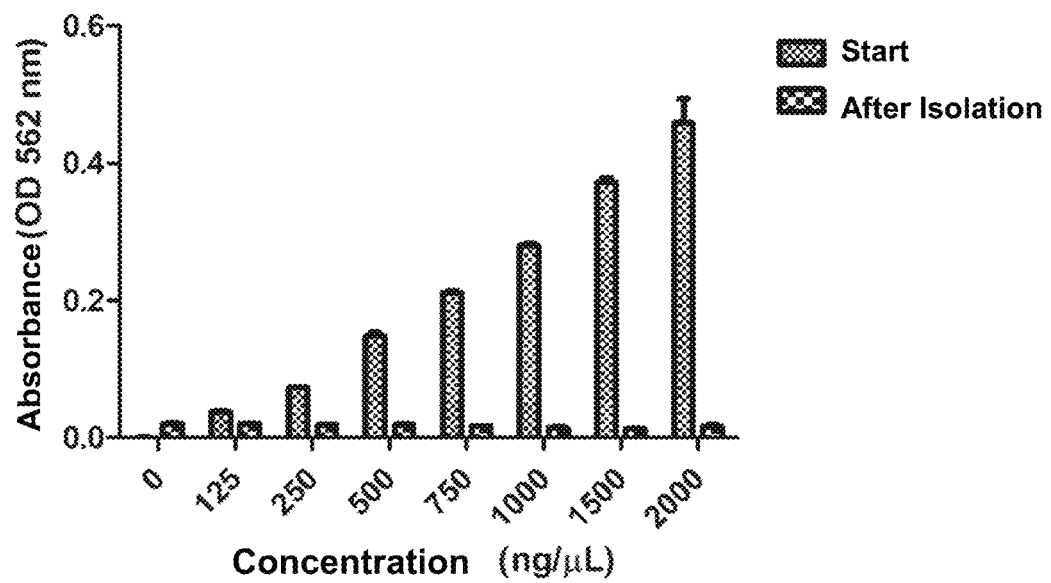
FIG. 4 is a graphical representation of the amounts of protein measured before and after exosome isolation of proteins of different concentrations with known amounts in order to show that the protein contaminants have been removed in the exosome isolation method of the present invention. (The proteins are removed by 98% after the isolation).
Figure 5:
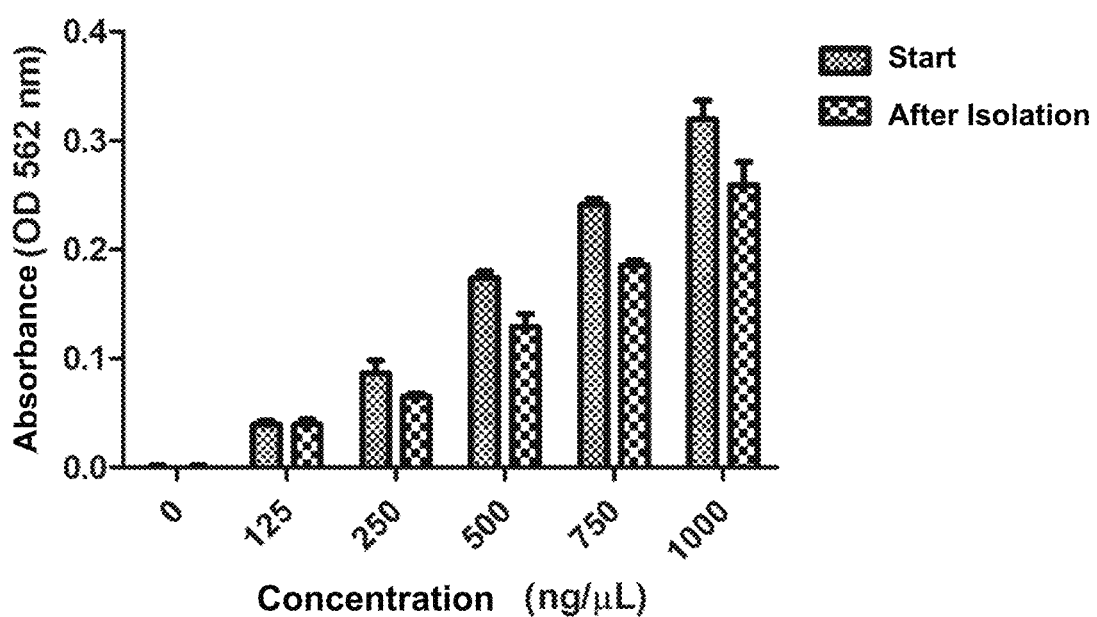
FIG. 5 is a graphical representation of the measurement of the amounts of exosomes before and after the isolation of the exosomes of different concentrations with known amounts in order to show that the exosomes have been isolated with high efficiency. (The exosomes are obtained with 80% efficiency after isolation).

A two-phase fluid system is used for separating the homogeneous exosome-protein mixture obtained as a result of the preparation steps. These systems are systems that are used to separate the molecules by forming a phase by utilizing the chemical and physical properties of the polymers they contain. Exosomes are cleared of nonexosomal proteins and other impurities by utilizing the chemical tendency of the PEG phase to the proteins and the DEX phase to the phospholipid structured membranes in the two-phase fluid system. Due to the concentration of the polymers used in the solution, it is determined that a maximum amount of protein remained in the PEG phase (FIG. 1), while the DEX phase contained a high amount of exosomes (FIG. 5).

After the first step of the two-phase separation process, the PEG phase reaches protein saturation, and thus washing process is performed to remove the contaminant proteins remaining in the DEX phase. Following withdrawal of the supernatant in the isolation process, the washing process is carried out by using the supernatant having the same physicochemical properties in order not to change the working concentration of the system. As a result, as there is no protein in the newly added PEG phase, the nonexosomal proteins in the DEX phase can migrate to the supernatant.

The exosome molecules that are commonly obtained in isolation and washing processes are in the DEX phase. Accordingly, it was observed that in both functional applications and in vesicle characterization and analyses, the DEX phase, in which the vesicles were present, influenced the experimental conditions. The dextran molecules in the solution are removed by the process of methanol precipitation in order to obtain the exosomes in pure form separate from the DEX phase. By making use of the nonsolubility of Dextran molecules in monohydric alcohols, Dextran molecules were precipitated by increasing the alcohol concentration in the solution and separated from the solution using centrifugation. In addition, due to the fact that the methanol remaining in the solution has a negative effect on the biological-based assays, it can be removed by making use of its low boiling point.

The invention is an isolation method for the isolation of exosomes. The exosome isolation process begins by mixing the said obtained materials (lysates) with isolation solutions as described above. The lysates obtained from the plants, blood plasma or cell culture media are mixed with the isolation solution, whose content is indicated in Table 1. This mixing process is performed by inverting about 20 times. Then the mixture is subjected to centrifugation. Centrifugation is carried out at 1,000 g for 10 minutes at +4° C. The mixture that is subjected to centrifugation is divided into two phases, namely the supernatant comprising 85-95% of the mixture containing proteins and other cellular residues and the lower phase comprising about 5% of the mixture in which the exosomes are collected. The supernatant is carefully removed and discarded. The lower phase containing the exosomes constitutes about 10% of the total mixture. To obtain ultra-pure exosome, centrifugation is repeated with the washing solution, whose content is given in Table 1. The dextran in the lower phase containing the exosomes can be removed depending on the content of the experiment that will be conducted. Dextran removal process can be carried out by filtering through a 1000-500 kilodalton filter and collecting the supernatant or by adding methanol thereby precipitating the dextran. The mixture obtained by adding methanol is mixed by inverting 10-15 times and then it is centrifuged at 12000-14000 g for 10-20 minutes at +2-+8° C. The supernatant is collected and the methanol in the exosome solution is evaporated by means of an evaporator. The exosomes can be aliquoted and stored at −80° C. for up to 12 months, or lyophilized and stored in powder form at +4° C. for up to 36 months.

Preparation of the Samples

Cell Culture Medium;

The medium collected from the cell culture is filtered through a 0.22 μm filter for removing microvesicles and cell parts.

The collected medium can be stored at 4° C. for up to 24 hours, at −20° C. up to one week, and for long term storage, at −80° C. up to one year.

Blood Plasma;

The collected blood plasma is filtered through a 0.22 μm filter for removing microvesicles and cell parts.

The obtained extract can be stored at 4° C. for 24 hours, at −20° C. for one week, and at −80° C. for long term storage.

Plant Lysate

The plant lysate which is homogenized by the help of a homogenizer or blender is filtered (preferably by a filter with a pore size of 150-400 μm).

It is centrifuged at 12000 g for 10 minutes at +4° C.
The supernatant is collected and filtered through a 0.22 nm filter.
The obtained extract can be stored at 4° C. for 24 hours, at −20° C. for one week, and at −80° C. for long term storage.

TABLE 1

Content information of the solutions used within the scope of the invention.

| Name | Molecular weight (Mw)/Molecular Mass (Mr) | Linear Formula | Solvent | Concentration (gram/liter) | Solution Type |
|---|---|---|---|---|---|
| PEG (Poly ethylene glycol) + Dextran | Mw 25000-45000 Mr 450000-650000 | $H(OCH_2CH_2)_nOH$ + $(C_6H_{10}O_5)n$ | $dH_2O$ | 3.35 + 1.65 | Isolation Solution |
| Poly (ethylene glycol) | Mw 25000-45000 | $H(OCH_2CH_2)_nOH$ | $dH_2O$ | 3.35 w/v | Washing Solution |

TABLE 2

The storage conditions off the solutions used within the scope of the invention.

| Name of the Product | Storage Conditions |
|---|---|
| Isolation Solution | +4° C. |
| Washing Solution | +4° C. |

TABLE 3

The amounts of the exosome obtained from 1 milliliter of the starting materials.

| Starting Material | Initial Amount | Exosome Amount |
|---|---|---|
| Cell Culture Medium | 1 mL | 50-250* μg |
| Blood Plasma | 1 mL | 50-300* μg |
| Plant Lysate | 1 mL | 10-250* μg |

(*The amount of exosome to be obtained may vary according to the Cell/Medium - Plant lysate/Solution - Blood Cell/Plasma ratio.)

TABLE 4

The amounts of RNA obtained from 1 microgram of exosome.

| Starting Material | Exosome | RNA |
|---|---|---|
| Cell Culture Medium | 1 μg | 10-150 ng |
| Blood Plasma | 1 μg | 10-250 ng |
| Bitki Lysate | 1 μg | 10-250 ng |

The advantages of the exosome isolation method of the present invention can be listed as follows:
It is inexpensive,
It is suitable for isolation in very small or large amounts,
Products are obtained in high purity without protein contamination,
Isolation from different materials (blood, cell culture medium, plants, mammalian tissues and all biomaterial) is possible,
Isolation process is easy,
It is possible to obtain high amounts of pure RNA,
It does not require high speed centrifugation such as 100,000 g,
It does not require long incubation periods,
Polymer staining solution is used to facilitate separation between the phases.

What is claimed is:
1. An exosome isolation method by a two phase fluid extraction system for obtaining exosomes from cytoplasm inner and outer fluids, comprising the steps of
preparing a fluid sample containing the exosomes,
removing contaminants in the fluid sample,
mixing the fluid sample with an isolation solution containing PEG and dextran to form a mixture for isolation,
separating the mixture for isolation into two phases by using the two phase fluid extraction system,
discarding a supernatant upper phase of the two phases formed in the mixture for isolation, in order to remove proteins and undesired substances therein,
removing dextran from the lower phase containing the exomes, wherein removing dextran comprises:
adding a purification solution containing monohydric alcohol or acetone to remove dextran from the lower phase containing the exosomes,
removing the dextran from the lower phase containing the exosomes via a filtration,
removing the dextran precipitated by the purification solution,
removing the purification solution from the exosomes and thereby obtaining exosomes in a pure form in a collected phase from the mixture for isolation;
mixing the collected phase from the mixture for isolation with a washing solution to form a mixture for washing,
separating the mixture for washing into two phases using the two phase fluid extraction system,
discarding a supernatant of the two phases formed in the mixture for washing and collecting a lower phase containing the exosomes.
2. The exosome isolation method according to claim 1, wherein the fluid sample containing the exosomes is a polar fluid.
3. The exosome isolation method according to claim 2, wherein the fluid sample containing the exosomes is a fluid selected from a group comprising cell culture media, blood, blood serum, blood plasma, placental fluid, saliva, urea, semen, breast milk, plant extract and mixtures thereof.
4. The exosome isolation method according to claim 1, wherein filtration is further used for removing large contaminants from the fluid sample.
5. The exosome isolation method according to claim 1, wherein a centrifugation method is used for removing large contaminants from the fluid sample.
6. The exosome isolation method according to claim 1, wherein a molecular weight of the PEG in the isolation solution is between 25,000 and 45,000 daltons.
7. The exosome isolation method according to claim 1, wherein a molecular weight of the Dextran in the isolation solution is between 450,000 and 650,000 daltons.

8. The exosome isolation method according to claim 6, wherein a concentration by mass of the PEG used in the isolation solution is between 2% and 4%.

9. The exosome isolation method according to claim 7, wherein a concentration by mass of the Dextran used in the isolation solution is between 0.75% and 2.80%.

10. The exosome isolation method according to claim 1, wherein a centrifugation method is used in the two phase fluid extraction system used for obtaining the exosomes.

11. The exosome isolation method according to claim 10, wherein the centrifugation method is performed at 1,000 g and 5,000 g in the two phase fluid extraction system used for obtaining the exosomes.

12. The exosome isolation method according to claim 1, wherein PEG in water is used as the washing solution.

13. The exosome isolation method according to claim 12, wherein the washing solution contains 2% to 4% by mass of the PEG.

14. The exosome isolation method according to claim 12, wherein a molecular weight of the PEG in the washing solution is between 25,000 and 45,000 daltons.

15. The exosome isolation method according to claim 1, wherein a centrifugation method is used for separating the washing solution into the two phases.

16. The exosome isolation method according to claim 1, wherein filtration is further used for removing microvesicles in the mixture of washing.

17. The exosome isolation method according to claim 1, wherein the monohydric alcohol in the purification solution used to precipitate the dextran is ethanol or methanol.

18. The exosome isolation method according to claim 1, wherein a mixing ratio of the monohydric alcohol and the lower phase containing the exosomes is in the range of 1:1 to 3:1 by volume.

19. The exosome isolation method according to claim 1, wherein a centrifugation method is used for removing dextran from the exosomes.

20. The exosome isolation method according to claim 1, wherein a pore diameter of a filter used in the filtration for removal of the dextran is smaller than a diameter of the exosomes and greater than a molecular diameter of dextran.

21. The exosome isolation method according to claim 1, wherein a pore diameter of a filter used in the filtration is in a range of 40 kilodaltons to 500 kilodaltons.

* * * * *